United States Patent [19]

Krajicek

[11] Patent Number: 5,303,718
[45] Date of Patent: Apr. 19, 1994

[54] METHOD AND DEVICE FOR THE OSTEOSYNTHESIS OF BONES

[76] Inventor: Milan Krajicek, No. 19, 5. Kvetna, 140 00, Praha 4, Czechoslovakia

[21] Appl. No.: 821,095

[22] Filed: Jan. 15, 1992

[51] Int. Cl.⁵ .............................................. A61B 19/00
[52] U.S. Cl. ..................................... 128/897; 606/60; 623/16
[58] Field of Search ........................ 128/897–899; 606/53, 60–63, 68, 74; 623/16, 17, 21, 22

[56] References Cited

U.S. PATENT DOCUMENTS

| | | | |
|---|---|---|---|
| 4,313,434 | 2/1982 | Segal | 606/62 |
| 5,037,445 | 8/1991 | Sander et al. | 623/16 |
| 5,102,413 | 4/1992 | Poddar | 606/62 |
| 5,108,404 | 4/1992 | Scholten et al. | 606/60 |

Primary Examiner—Lee S. Cohen
Assistant Examiner—John P. Lacyk
Attorney, Agent, or Firm—Panitch Schwarze Jacobs & Nadel

[57] ABSTRACT

A device for osteosynthesis of bones by intra-marrowial fixation includes a tube (2) made of a non-elastic material, adapted to be inserted into the marrow cavity of a bone (1), one end (2') being sealed, and the other end being open, and a connection part (13), comprising a fixation part (4) designed to be inserted into the tube (2) for the fixation of the tube (2) in a hole of the bone (1), and a vent part (12) designed to be inserted into the fixation part (4) and for a tight connection therewith, and including a connection (8) for a line (14) for introducing a pressurized biologically inert liquid (10) into the tube (2) and releasing it therefrom, and a valve (9) for opening and closing the liquid passage through the vent. The tube (2) is filled with a biologically unobjectionable sterilizable liquid (10), for example water, gelatin solution or dextran solution, under a pressure of 200 to 1000 kPa.

22 Claims, 2 Drawing Sheets

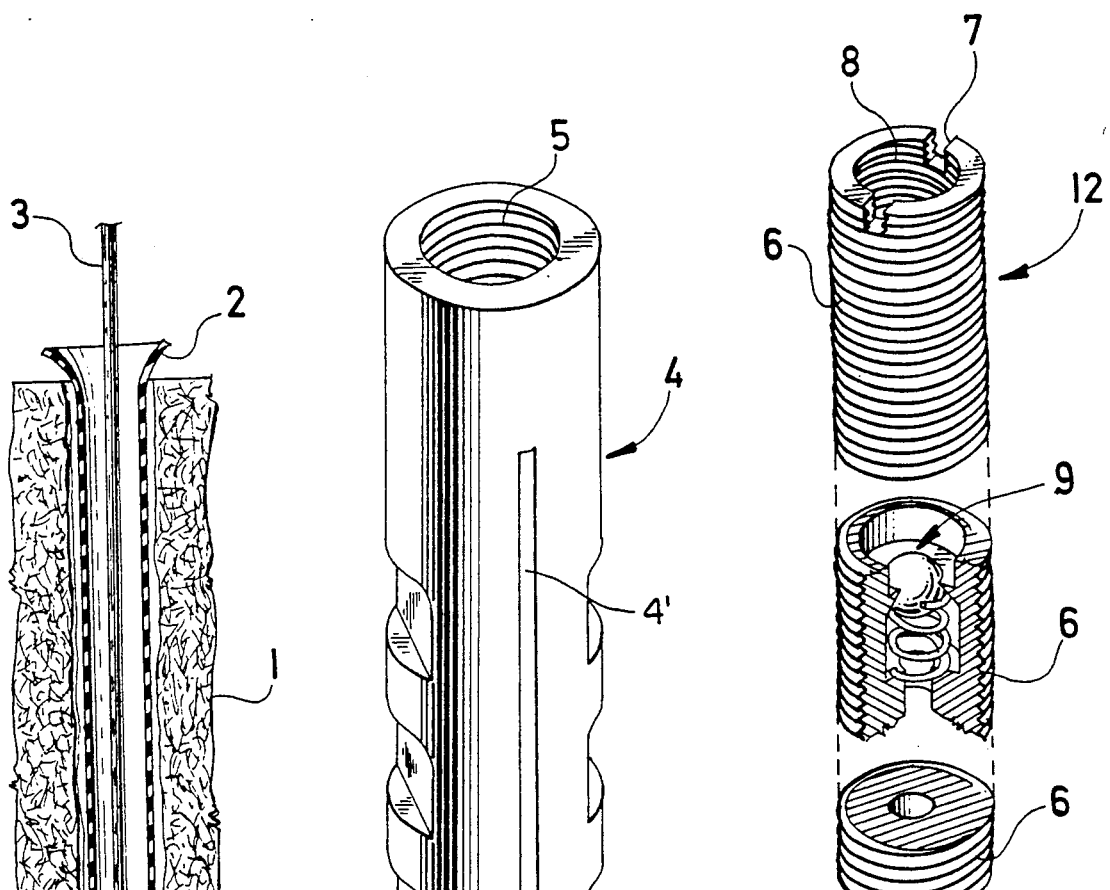

METHOD AND DEVICE FOR THE OSTEOSYNTHESIS OF BONES

FIELD OF THE INVENTION

The present invention relates to a method and a device for the osteosynthesis of bones by the method of intramarrowial cavity fixation.

BACKGROUND OF THE INVENTION

For the osteosynthesis of bones, i.e. the connection of fragments of bones through surgical methods, usually different kinds of wires, splints, etc., are used for external osteosynthesis. On the other hand, for the so-called intra-marrowial cavity osteosynthesis, a solid metal rod is introduced into the marrow cavity of the respective bone over its whole length, thereby stabilizing the fragments during the whole period necessary for the natural healing process. For this type of intra-marrowial osteosynthesis, a lot of different kinds and types of nails and rods has been developed, differing in their shape, form and size and the materials used.

There is no question that a correctly executed intramarrowial osteosynthesis has a lot of advantages; however, there are also a few, but relevant disadvantages. This applies particularly for the most common method of open nailing. For this method, a relatively extensive instrumentarium is necessary, which also makes this method complex and expensive, since a broad variety of nails and rods are to be provided in view of the individual adaptation to the patient. This procedure is also time-consuming, particularly in cases when holes are to be drilled into the marrow cavity of the bone prior to the nailing, which also increases the risk of infections. Another disadvantage of this method is that the nails or rods fixed to the bone must be removed after the healing of the bone, i.e. usually within a period of about two months to about two years after application, which by itself is also a relatively demanding procedure.

SUMMARY OF THE INVENTION

It is the object of the present invention to provide a method and a device for the osteosynthesis of bones by the intra-marrowial method which overcome the above mentioned disadvantages of the prior art, simplify the whole procedure of osteosynthesis and allow a considerable reduction of the irradiation dose of the surgical team because of a substantially simpler application and removal of the device, requiring a relatively simple and universal instrumentarium, and involving a considerable lower risk of infections.

The above object is achieved according to the main claims. The dependent claims relate to preferred embodiments of the concept of the present invention.

The device according to the present invention for the osteosynthesis of bones by the intra-marrowial method is characterized by a tube made of a non-elastic, strong but pliable and biologically inert, sterilizable material, provided to be inserted into the marrow cavity of a bone, one end being sealed, and the other end being open, and a connection part, comprising a fixation part designed to be firmly inserted into the open end of the tube for the fixation of the tube in an access hole of the bone to the marrow cavity and for a tight connection with the tube, and a vent part designed to be firmly inserted into the fixation part and for a tight connection therewith, and comprising means for connecting a line for introducing a pressurized biologically inert, sterilizable or sterilized liquid into the tube and releasing it therefrom, and valve means for opening and closing the liquid passage therethrough, preferably a returnable ball vent, and possibly comprising the biologically inert, sterilizable or sterilized liquid contained in the tube.

The method of the present invention—which can also be used without relation to the surgical or therapeutical treatment of the human and animal body, for example for research and development purposes, animal tests, etc.—is characterized by the following steps:

Inserting a tube made of a non-elastic, strong but pliable and biologically inert, optionally sterilized material, one end of which being sealed, and the other end being open, into the marrow cavity of a bone by means of an insertion instrument, preferably made of a metal or metal alloy, and preferably being rod-like and having a rounded end, introducing a fixation part designed to be firmly inserted into the open end of the tube for the fixation of the tube in the access hole of the bone to the marrow cavity and for tight connection with the tube, cutting the surplus part of the tube, introducing a vent part into the fixation part and firmly and tightly fixing it in the fixation part, the vent part comprising means for connecting a line for introducing a pressurized liquid, preferably being biologically inert, sterilizable or sterilized, into the tube and releasing it therefrom, and comprising valve means for opening and closing the liquid passage therethrough, preferably a returnable ball vent, introducing the pressurized liquid into the tube, preferably at a pressure of 200 to 1000 kPa, and closing the valve means and disconnecting the line from the vent part, and optionally connecting the line to the vent part and releasing the liquid contained in the tube, and withdrawing the tube from the marrow cavity of the bone through the access hole.

According to a preferred embodiment of the device, the fixation part has a dowel-like form and is expandable, e.g. by inserting the vent part from its uncut end for fixing it in the access hole of the bone and for a tight connection with the tube.

The cut portion of the dowel-like fixation part preferably comprises at least one longitudinal slot, these slots preferably being regularly arranged over the circumference.

In accordance with another advantageous embodiment, the fixation part of the device comprises an internal thread, and the vent part comprises an external thread fitting into the internal thread of the fixation part, the vent part preferably being provided with a slot groove at its outer end.

Alternatively, in accordance with a further preferred embodiment, the internal portion of the fixation part and the outer portion of the vent part are designed to form a bayonet joint for tight fixation of the vent part in the fixation part.

The means for connecting the liquid line to the vent part preferably are an internal thread provided in the vent part, a flange or a sleeve.

The tube of the device is preferably made of or comprises polyethylene, polyurethane and/or polytetrafluoroethylene. The fixation part is preferably made of a solid, inert and sterilizable material, advantageously of a metal or a metal alloy.

In accordance with yet another advantageous embodiment, the device according to the present invention further comprises means for pressurizing and supplying and draining the filling liquid, designed to be connected via the liquid line to the vent part of the connection part, for filling the tube at a predeterminable pressure, preferably within the range of 200 to 1000 kPa, and to be disconnected therefrom.

The liquid used for filling the tube is preferably a biologically inert, sterilizable liquid, advantageously water, a gelatine solution or a dextran solution. It may optionally comprise a radio-opaque material, preferably an iodine or an iodide solution, for producing a sufficient X-ray contrast.

The present invention also comprises kits of parts, comprising a device as defined above and a biologically inert, sterilizable or sterilized liquid provided to be introduced into the tube of the device and to be released therefrom after the healing period of the bone. These kits of parts may further comprise means for pressurizing and releasing the liquid through a line connectable to the vent part of the device, preferably comprising pumping means such as a peristaltic pump, a liquid reservoir, valves and a pressure gauge.

The basic advantage of the concept of the present invention is the application of the physical principle of non-compressibility of liquids. For inserting the tube into the bone, only one access hole is to be drilled into the marrow cavity, and then the tube made of a nonelastic, pliable material is inserted through the access hole by means of an insertion instrument preferably made of a metal or a metal alloy, and preferably being rod-like and having a rounded end. After insertion, the tube is fixed in the access hole of the bone, e.g. by the dowel-like fixation part into which the vent part is firmly inserted thereafter. Subsequently, the system is filled under a predetermined pressure, preferably using a biologically inert liquid as defined above. During the filling procedure, the necessary rearrangement and adjustment of the bone fragments may be performed, which represents a considerable advantage. When the predetermined maximal pressure within the tube inside the marrow cavity of the bone has been reached, a perfect cast has been formed, the stability and tenacity of which is comparable to any type of nail and/or rod fixation.

The removal of the device after the healing period is very simple, because after release of the liquid, the other parts of the device, i.e. the connection part and the tube, may be removed without any problem. In comparison with all presently used kinds of intramarrowial osteosynthesis, the device according to the present invention leads to a significant simplification of the whole procedure, which is of highest surgical and therapeutical value because the operation time can be significantly reduced, less drillings of bones are necessary, the total instrumentarium is extremely simple and universally applicable, and the infection risks are minimized particularly due to the reduction of the surgical operation time and the reduced number of drillings. Furthermore, the substantial reduction of costs involved leads to considerable savings regarding both the method and the device and materials.

BRIEF DESCRIPTION OF THE DRAWINGS

In the following, the invention will be explained in more details with reference to the accompanying drawings, relating to a preferred embodiment of the device according to the present invention.

FIG. 1 is a schematic representation of the non-elastic, pliable but strong tube with sealed lower end, introduced into the marrow cavity of a bone;

FIG. 2 is a schematic representation of a dowel-like fixation part for the fixation of the tube in the access hole to the marrow cavity of a bone;

FIG. 3 is a schematic representation of the vent part of the device;

DESCRIPTION OF THE PREFERRED EMBODIMENTS

Figures 4, 5:
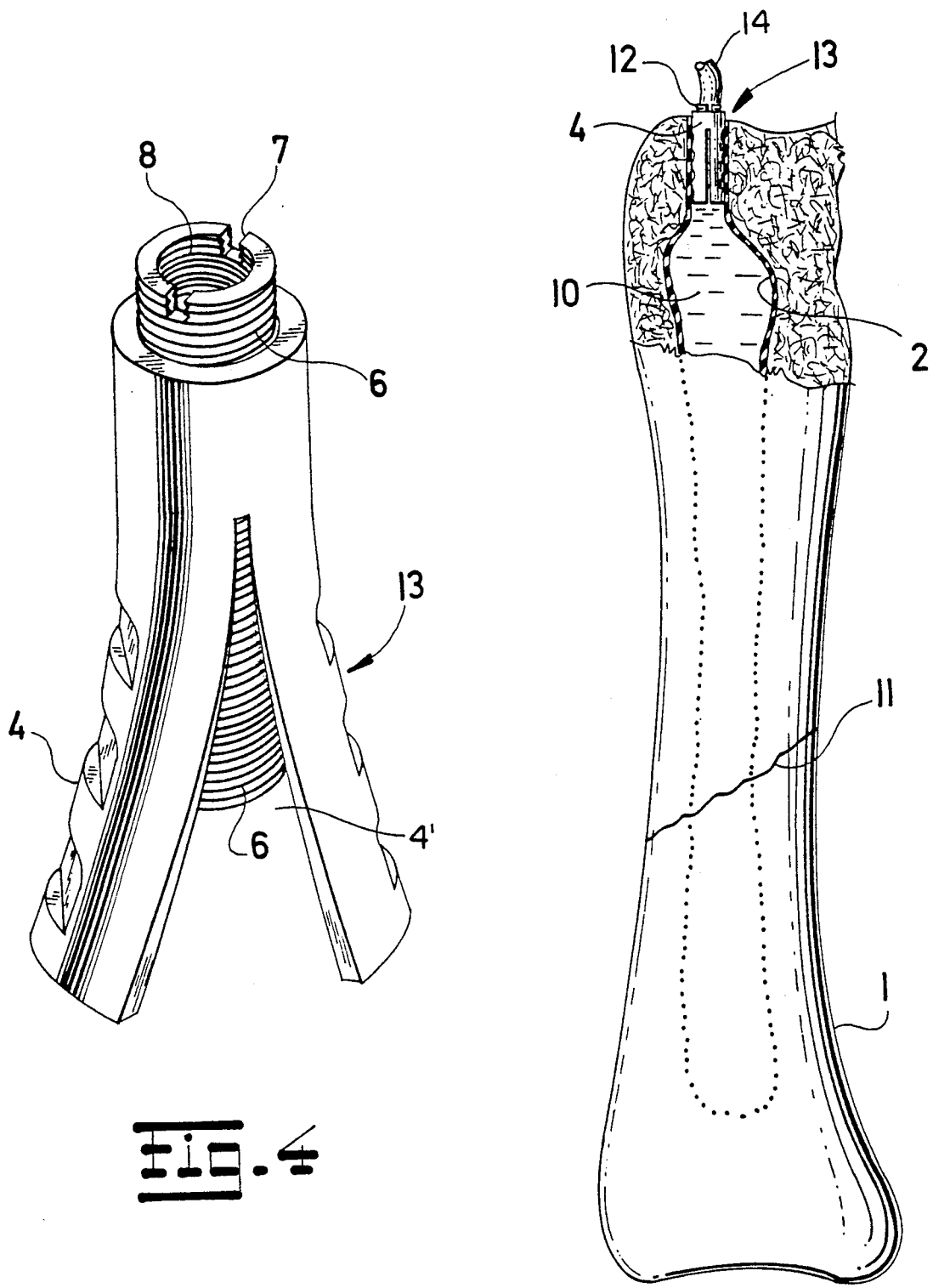
FIG. 4 is a schematic representation of the complete connection part comprising the fixation part and the vent part, allowing the inflow and the outflow of a liquid, the vent part and the fixation part being the same as shown in FIGS. 2 and 3, respectively.
FIG. 5 is a schematic representation of the device of the present invention introduced into a long bone with a transversal fracture.

As may be seen from FIGS. 1 to 4, the device comprises a tube 2 made of a non-elastic, pliable but strong material. The tube 2 may be inserted by means of an insertion instrument 3 into the marrow cavity of a bone 1.

The tube 2 is preferably made from a biologically inert, sterilized material, for example of polyethylene, polyurethane and/or polytetrafluoroethylene. One end 2' of the tube 2, i.e. the internal end, is sealed, and the other end is open. Into the open end of the tube 2, the fixation part 4 is introduced for the fixation of the tube in the bone 1, and for a firm connection to the fixation part. The fixation part 4 as shown in FIG. 2 comprises a longitudinal slot, allowing an expansion of the dowel-like fixation part, as may be seen from FIG. 4. The vent part 12 shown in FIG. 3 is firmly insertable into the fixation part 4, thus forming the connection part 13 of the device of the present invention, which allows the inflow and outflow of a filling liquid. During the procedure of osteosynthesis, the tube 2 is filled with a biologically inert, unobjectionable sterile liquid 10, for example water, gelatine solution or dextran solution, advantageously under a pressure of 200 to 1000 kPa.

The fixation part 4 is preferably dowel-like, as shown in FIGS. 2 and 4, and its non-cut end is provided with an internal thread 5 fitted to the external thread 6 of the vent part 12. The cut end of the fixation part 4 is provided with at least one longitudinal slot 4', these slots preferably being regularly distributed along the circumference of the fixation part 4. In view of the drilling of a hole into the bone to be fixed, the fixation part 4 and the vent part 12 of the connection part 13 preferably are of round, mainly cylindrical shape.

The fixation part 4 is preferably made of a metal, solid, inert and sterilizable material. The external thread 6 of the vent part 12 serves for screwing the vent part 12 into the internal thread 5 of the fixation part 4. The vent part 12 is further provided on its outer end with a slot groove 7 and comprises an internal thread 8 for the line 14 (FIG. 15) for the liquid 10. The line 14 may be connected to the means for pressurizing and releasing the filling liquid 10. The vent part 12 comprises a vent 9 which advantageously is a returnable ball vent. The vent 9 is preferably provided in the middle part of the vent part 12.

Instead of the connection of the fixation part 4 and the vent part 12 by means of a screw-like mechanism, it is possible to provide a bayonet joint connection for the fixation of the vent part 12 in the fixation part 4, the internal portion of the fixation part 4 and the outer portion of the vent part 12 being correspondingly adapted to each other. The tube 2 is filled with the liquid 10, preferably comprising a radio-opaque material, for example an iodine solution.

As may be seen from FIG. 5, the non-elastic, pliable but strong tube 2 with sealed internal end is introduced into the marrow cavity of a bone 1 having a transversal fracture 11. This tube 2 is inserted by means of the insertion instrument 3 (FIG. 1), advantageously made of a metal or metal alloy. The fixation part 4 of dowel-like form is then inserted into the open end of the tube, wherein the pressure exerted by the preferably expanded fixation part guarantees the firm fixation of the tube 2 in the access hole of the bone 1 and the tight connection between the tube 2 and the fixation part 4. After the insertion of the fixation part, the surplus part of the tube 2 is cut off. Subsequently, the vent part 12 provided with an external thread 6 is firmly screwed into the internal thread 5 of the fixation part 4. The screwing of the vent part 12 into the fixation part 4 may be facilitated by the slot groove 7 provided at the outer end of the vent part 12. The vent part 12 comprises in that end portion an internal thread 8 into which a line, flange or sleeve may be screwed in for connecting the line 14 for the liquid 10 from and to a pressure pump. The vent part 12 is further provided with the vent 9, for example with a returnable ball vent. According to this embodiment, the vent part 12 also provides the internal mechanism for expanding the dowel-like fixation part 4 by screwing-in.

As may be seen from FIG. 5, the device according to the present invention may also be inserted into long bones 1 having a transversal fracture 11 because the length of the tube 2 may be easily adapted to the respective length of the marrow cavity of the bone 1. This represents a considerable further advantage of the present invention because only one kind of tubes may be used for very different kinds of bones, by simply cutting the surplus tube at the end of the access hole. FIG. 5 shows the fixation of the tube 2 in the access hole of the bone 1 by means of the fixation part 4 of the connection part 13. FIG. 5 further shows the line 14 through which the liquid 10 is introduced into the tube 2 and released therefrom after the healing period, prior to simply withdrawing the tube through the access hole. The connection part 13 accordingly allows an easy inflow and outflow of the filling liquid 10 which is introduced for osteosynthesis under a predetermined, suitable pressure.

The tube 2 of the device of the present invention forms, after insertion into the bone, a kind of solid mould, with an ideal adaptation of its shape to the natural internal form of the marrow cavity. After the filling procedure the line 14 to the pressure pump is disconnected from the connection part 13. After the fracture 11 is healed, the whole device may be easily removed from the bone after release of the liquid 10.

Thus, the concept of the present invention represents a significant technological and surgical advance in the field of osteosynthesis.

I claim:

1. Device for the fixed osteosynthesis of bones by the intra-marrowial method, comprising:
   a tube (2) made of a non-elastic, strong but pliable and biologically inert, sterilizable material, adapted to be inserted into the marrow cavity of a bone (1), one end (2') being sealed, and the other end being open, and
   a connection part (13), comprising:
      fixation means (4) designed to be firmly inserted into the open end of the tube (2) to adaptively fixate the tube (2) to an access hole of the bone (1) to the marrow cavity and for a tight connection with the tube (2), and
      vent means (12) designed to be firmly inserted into the fixation means (4) and for a tight connection therewith, and comprising a liquid passage through said vent means, means (8) for connecting a line (14) for introducing a pressurized biologically inert, sterilizable or sterilized liquid (10) into the tube (2) and for releasing the liquid from the tube through said liquid passage, and valve means (9) for opening and closing the liquid passage.

2. The device according to claim 1, wherein the fixation means (4) has a cylindrical shape having an uncut end and a cut portion, the cut portion being expandable by inserting the vent means (12) into the uncut end for adaptively fixing the tube in an access hole of the bone (1) and for a tight connection of the fixation means with the tube (2).

3. The device according to claim 2, wherein the cut portion of the fixation means (4) comprises at least one longitudinal slot (4').

4. The device according to claim 1, wherein the fixation means (4) comprises an internal thread (5), and the vent means (12) comprises an external thread (6) fitting into the internal thread (5) of the fixation means (4).

5. The device according to claim 4 wherein the vent means (12) is provided with a slot groove (7) at an outer end of the vent means.

6. The device according to claim 1, wherein an internal portion of the fixation means (4) and an outer portion of the vent part (12) are designed to form a bayonet joint for tight fixation of the vent part (12) in the fixation means (4).

7. The device according to claim 1, wherein the means (8) for connecting the line (14) are an internal thread, a flange or a sleeve.

8. The device according to claim 1, wherein the tube (2) comprises polyethylene, polyurethane and/or polytetrafluoroethylene.

9. The device according to claim 1, wherein the fixation means (4) is made of a metal or a metal alloy.

10. The device according to claim 1, wherein it further comprises means for pressurizing and supplying and draining the liquid (10), designed to be connected via the line (14) to the vent part (12) of the connection means (13), for filling the tube (2) at a predeterminable pressure, and to be disconnected therefrom.

11. The device according to claim 10 wherein the predeterminable pressure is from about 200 to about 1,000 kPa.

12. The device according to claim 1 wherein the biologically inert, sterilizable liquid (10) is water, a gelatine solution or a dextran solution.

13. The device according to claim 12 wherein the biologically inert, sterilizable liquid further comprises a radio-opaque material.

14. The device according to claim 13 wherein the radio-opaque material is iodine or an iodine solution.

15. The device according to claim 1 wherein the valve means (9) is a returnable ball vent.

16. The device according to claim 1 further comprising a biologically inert, sterilizable or sterilized liquid (10) contained in the tube (2).

17. A method for the fixed osteosynthesis of bones by means of intra-marrowial fixation, comprising:

inserting a tube (2) made of non-elastic, strong but pliable and biologically inert, material one end of which (2') being sealed, and the other end being open, into the marrow cavity of a bone (1) my means of an insertion instrument (3), introducing a fixation part (4) into the open end of the tube (2) for the fixation of the tube (2) in an access hole of the bone (1) to the marrow cavity the fixation part being tightly connected with the tube (2), cutting a surplus part of the tube (2), introducing a vent part into the fixation part (4) and firmly and tightly fixing it in the fixation part (4), the vent part (12) comprising a liquid passage through said vent part, means (8) for connecting a line (14) for introducing a pressurized liquid (10), into the tube (2) and for releasing the liquid from the tube through said liquid passage, and valve means (9) for opening and closing the liquid passage, introducing the pressurized liquid (10) into the tube (2) through the liquid passage, and closing the valve means (9) and disconnecting the line (14) from the vent part (12), and withdrawing the tube (2) from the marrow cavity of the bone (1) through the access hole.

18. The method according claim 17 wherein the non-elastic, strong but pliable and biologically inert material is sterilized.

19. The method according to claim 17 wherein the pressurized liquid (10) is biologically inert, sterilizable or sterilized.

20. The method according to claim 17 wherein the pressurized liquid is introduced at a pressure of about 200 to about 1,000 kPa.

21. The method according to claim 17 wherein after disconnecting the line (14) and before withdrawing the tube (2), the line (14) is reconnected to the vent part (12) and the liquid (10) contained in the tube (2) is released.

22. A kit for a device for the fixed osteosynthesis of bones by the intra-marrowial method, comprising:

a tube (2) made of a non-elastic, strong but pliable and biologically inert, sterilizable material, adapted to be inserted into the marrow cavity of a bone (1), one end (2') being sealed, and the other end being open, and a connection part (13), comprising:

a fixation part (4) designed to be firmly inserted into the open end of the tube (2) to adaptively fixate the tube (2) to an access hole of the bone (1) to the marrow cavity and for a tight connection with the tube (2), and a vent part (12) designed to be firmly inserted into the fixation part (4) and for a tight connection therewith, and comprising a liquid passage through said vent part, means (8) for connecting a line (14) for introducing a pressurized biologically inert, sterilizable or sterilized liquid (10) into tube (2) and for releasing the liquid from the tube through said liquid passage, and valve means (9) for opening and closing the liquid passage; and a biologically inert sterilizable or sterilized liquid (10) for introduction into the tube (2) of the device.

* * * * *